US 6,723,347 B1

(12) United States Patent
Yamagata et al.

(10) Patent No.: US 6,723,347 B1
(45) Date of Patent: Apr. 20, 2004

(54) PROCES FOR PRODUCING PROTEIN POWDER

(75) Inventors: Yutaka Yamagata, Kobe (JP); Takayuki Doen, Suita (JP); Naoki Asakawa, Takatsuki (JP); Shigeyuki Takada, Nishimoniya (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 10/088,142

(22) PCT Filed: Sep. 14, 2000

(86) PCT No.: PCT/JP00/06303
§ 371 (c)(1),
(2), (4) Date: Mar. 15, 2002

(87) PCT Pub. No.: WO01/21187
PCT Pub. Date: Mar. 29, 2001

(30) Foreign Application Priority Data

Sep. 17, 1999 (JP) .......................................... 11-263048

(51) Int. Cl.$^7$ ................................................ A61K 9/14
(52) U.S. Cl. .................... 424/489; 424/484; 514/772.4; 514/964; 514/2
(58) Field of Search ................................ 424/489, 484; 514/772.4, 964, 2

(56) References Cited

U.S. PATENT DOCUMENTS

| | | | |
|---|---|---|---|
| 3,607,858 A | 9/1971 | Querry | |
| 5,534,269 A | 7/1996 | Igari et al. | |
| 6,087,324 A | 7/2000 | Igari et al. | |
| 6,191,107 B1 * | 2/2001 | Yamagata et al. | ............. 514/12 |
| 6,197,350 B1 | 3/2001 | Yamagata et al. | |
| 6,267,981 B1 | 7/2001 | Okamoto et al. | |
| 6,482,864 B1 * | 11/2002 | Yamagata et al. | ....... 514/772.4 |

FOREIGN PATENT DOCUMENTS

| | | |
|---|---|---|
| JP | 05-194194 | 8/1993 |
| JP | 09-095440 | 4/1997 |
| JP | 9-248177 | 9/1997 |
| JP | 09-248177 | 9/1997 |
| WO | 90/13285 | 11/1990 |
| WO | 94/12158 | 6/1994 |
| WO | 95/29664 | 11/1995 |
| WO | 96/07399 | 3/1996 |
| WO | 97/01331 | 1/1997 |
| WO | WO 97/01331 * | 1/1997 |
| WO | 99/48519 | 9/1999 |

OTHER PUBLICATIONS

David E. Overcashier et al., "Preparation of Excipient–Free Recombinant Human Tissue–Type Plasminogen Activator by Lyophilization from Ammonium Bicarbonate Solution: An Investigation of the Two–Stage Sublimation Phenomenon" in *Journal of Pharmaceutical Sciences*, vol. 86, No. 4, Apr. 1997, pp. 455–459.

Yuh–Fun Maa et al., "Spray–Drying of Air–Liquid Interface Sensitive Recombinant Human Growth Hormone" in *Journal of Pharmaceutical Sciences*, vol. 87, No. 2, Feb. 1998, pp. 152–159.

Yohji Ohhashi, Seizai–To–Kikai (Pharmaceutical Preparation and Machines) "Recent Lyophilization Technology in Pharmaceuticals" pp. 6–8 (in Japanese with partial English translati n attached).

* cited by examiner

*Primary Examiner*—Thurman K. Page
*Assistant Examiner*—Rachel M. Bennett
(74) *Attorney, Agent, or Firm*—Wenderoth, Lind & Ponack, L.L.P.

(57) ABSTRACT

A process for conveniently producing a stable protein powder retaining the higher-order structure at a high level which comprises freezing a protein-containing solution at a cooling rate of about −300 to −10° C./min. and then drying.

16 Claims, 1 Drawing Sheet ent and a sustained-release preparation comprising the protein powder. Further, it relates to a sustained-release preparation comprising a specific base material, and the like.

PROCES FOR PRODUCING PROTEIN POWDER

This application is a 371 of PCT/JP00/06303 filed Sep. 14, 2000.

TECHNICAL FIELD

The present invention relates to a process for producing a protein powder and a sustained-release preparation comprising the protein powder. Further, it relates to a sustained-release preparation comprising a specific base material, and the like.

BACKGROUND ART

Recently, a large amount of proteins have been produced by utilizing Escherichia coli, yeasts, animal cells, or living bodies such as goat, hamsters, etc. due to developed genetic engineering and cell technology, and put to medicinal use. However, since these proteins have very high reactivity to acidic conditions and peptic enzymes, they are not absorbed by oral administration. Then, in general, they are administered subcutaneously or intramuscularly. However, they must be frequently administered because of the generally short biological half-life. The repeated injections takes a significant physical burden on patients.

For example, a growth hormone (hereafter sometimes referred to as GH), a representative hormone which is originally produced and secreted in the anterior portion of the pituitary gland, is a protein having widely diverse physiological activities such as promotion of growth in the body, metabolism of glucose and lipids, anabolism of protein, and cell proliferation and differentiation. And GH is recently produced on a large scale by utilizing Escherichia coli in genetic recombination technology field, and put to medicinal use clinically and worldwidely. However, GH must be frequently administered in order to maintain an effective blood level because of the short biological half-life. Especially, in the case of pituitary dwarfism, a daily subcutaneous administration to infants or young patients over a long period of time ranging from a few months to 10 years or more is conducted practically.

In order to deal with such specific problems of protein medicaments, various researches have been made for drug delivery systems. An example of the systems is a sustained-release preparation which lasts a release of a protein over a long period of time. JP-A 8-217691 (WO 96/07399) discloses a process for producing a sustained-release preparation which comprises a water-insoluble or slightly water-soluble polyvalent metal salt prepared by using a water-soluble peptide type of physiologically active substance and an aqueous solution of zinc chloride, etc., and a biodegradable polymer. Further, JP-A 8-503950 (WO 94/12158) discloses, as a process for producing a sustained-release preparation comprising human GH (hereafter sometimes referred to as hGH) and a biodegradable polymer, a process for producing microcapsules as porous particles by spraying an organic solvent solution of hGH and a polymer into liquid nitrogen, with biological activity retained. Furthermore, JP-A 10-504017 (WO 95/29664) discloses a process for producing sustained-release microcapsules by dispersing solid zinc carbonate, etc. in a polymer solution, and then adding a physiologically active substance (hormone, etc.) thereto to disperse the physiologically active substance and a metal cation separately in a biodegradable polymer. Although JP-A (WO 98/27980) and JP-A 10-7538 (WO 97/01331) disclose a process for producing sustained-release preparation comprising a physiologically active polypeptide, no condition for lyophilizing the physiologically active polypeptide is disclosed.

Thus, many attempts have been made for constructing drug delivery systems with retaining physiological activity of a protein. However, as problems specific for a protein having a higher-order structure, there are possible problems relating to stability of the protein which are resulted from denaturation during production steps of a preparation, denaturation due to change the protein with time in a preparation, and/or in vivo denaturation after administration, etc. Specifically, there is a possibility that problems of a sustained-release preparation such as low efficiency of protein uptake into a preparation, excess release of a drug at an initial stage of administration, difficulty in drug release control over a long period of time, low blood level of a drug after administration of a preparation, etc., remain unsolved.

However, where a protein can be prepared in the form of a finely divided powder, further improvement of stability of the protein is expected because of decrease in molecular mobility.

JP-A 4-500527 (WO 90/13285) discloses a process for producing a finely divided protein powder by spraying an aqueous solution of the protein into liquefied gas to freeze the solution and then drying.

In addition, Journal of Pharmaceutical Science, Vol. 87, p 152 (1998) reports a process for producing a finely divided protein powder by spray drying. However, this report discloses that denaturation degree is increased reversely correlating with the particle size of aqueous protein solution particles formed by spraying, and a large amount of a surfactant should be added to control it.

Further, WO 99/48519, which has been published after the priority date of the present application, discloses a process for producing a physiologically active polypeptide powder by adding a water-miscible organic solvent and/or a volatile salt to an aqueous solution of the physiologically active polypeptide and lyophilizing the solution.

Furthermore, JP-A 9-248177 discloses a process for producing dried microbial cells by dropping droplets of a microbial cell culture on a metal plate cooled below the freezing point to freeze cells quickly.

In general, a cooling rate of lyophilization is slower than −10° C./min. For example, Iyakuhin no Toketsukanso (Lyophilization of Medicines) (Yoji OHOHASHI, Preparations and Machines, page 8, Jan. 15, 1988, published by Crest, Co., Ltd.) describes as follows. "In lyophilization with a normal vial, to subject to quick freezing, or to use a solution containing a saccharide at such a high concentration that it forms a glassy state is not so often encountered unless a special apparatus is used. Namely, a cooling rate is 0.3 to 5° C./min." On the other hand, in case of spraying an aqueous solution into liquefied gas such as liquid nitrogen, etc., a cooling rate is extremely fast, e.g., faster than −300° C./min. in case of liquid nitrogen.

The minus sign in a cooling rate used herein is simply intended to express cooling. Therefore, for example, the cooling rate of −300° C./min. indicates that a material to be determined is cooled by 300° C. per 1 minute and, when a material to be determined is cooled by 150° C. in 30 seconds, the cooling rate is indicated as −300° C./min. More specifically, when a material to be determined is cooled from 20° C. to −130° C. in 30 seconds, the cooling rate is indicated as −300° C./min.

Like spray drying, in a process for producing a protein powder comprising spraying a solution of the protein into liquefied gas, freezing the solution and then drying, there is a high possibility that denaturation of the protein is caused. Further, since liquefied gas is used as a liquid refrigerant, large scale and expensive facilities are required for coping with heat insulation and expansion and contraction of materials of an apparatus due to difference in temperature, maintaining aseptic conditions, evacuating the liquefied gas, etc.

In addition, although a finely divided protein powder product having an average particle size of several microns can be obtained by using a large amount of a surfactant, use of the product is restricted because of the use of a large amount of a surfactant.

Then, it is desired to simply and conveniently provide a stable protein powder which retains a higher-order structure thereof without contact with liquefied gas.

DISCLOSURE OF INVENTION

The present inventors studied to solve the above problems, and found out the fact that a protein powder retaining its higher-order structure can be obtained by controlling a cooling rate for freezing a protein-containing solution, when producing the protein powder. Further, the present inventors found out the fact that a finely divided powder can be obtained by atomizing the above-obtained protein powder. In addition, the present inventors found out the fact that, when the above-obtained protein is used for the production of a sustained-release preparation, a protein entrapment ratio of the preparation, excess release of a drug at an initial stage of administration, and sustained release property can be improved.

Also, the present inventors found out the fact that a protein powder highly retaining its higher-order structure can be obtained with controlling a cooling rate by applying or dropping a protein-containing solution when freezing the solution.

Further, the present inventors found out the fact that the desired product can be obtained cheaper and more simply and conveniently by carrying out the above freezing using a shelf of a freeze-dryer normally used in lyophilization of medicaments.

Based on these findings, the present inventors accomplished the present invention.

That is, the present invention relates to:

(1) A process for producing a protein powder which comprises contacting a protein-containing solution with a refrigerant carrier, freezing the solution at a cooling rate of about −300 to −10° C./min. and then drying;
(2) The process according to the above (1), wherein the protein-containing solution is applied to or dropped on the refrigerant carrier;
(3) The process according to the above (2), wherein a dropping fluid of about 0.1 to 40 mm diameter is applied or dropped;
(4) The process according to the above (1), wherein freezing is carried out by preventing the protein-containing solution from direct contact with a liquid refrigerant;
(5) The process according to the above (1), wherein a volatile salt or water-miscible organic solvent is added to the protein-containing solution;
(6) The process according to the above (5), wherein the volatile salt is ammonium acetate;
(7) A protein powder obtainable by the process according to the above (1);
(8) The protein powder according to the above (7), wherein the protein has a molecular weight of about 5,000 to 1,000,000 dalton;
(9) The protein powder according to the above (7), wherein the protein is selected from hormones, cytokines, hematopoietic factors, growth factors and enzymes;
(10) The protein powder according to the above (7), wherein the protein is a growth hormone or insulin;
(11) The protein powder according to the above (7), wherein the protein retains 45% or more of α-helix based on the total α-helix content in the protein-containing solution;
(12) A process for producing a finely divided protein powder which comprising atomizing the protein powder according to the above (7);
(13) The process according to the above (12), wherein the atomization is carried out so that a finely divided protein powder having an average particle size of about 0.5 to 20 μm is obtained;
(14) A sustained-release preparation which comprises the finely divided protein powder obtained by the process according to the above (12);
(15) The sustained-release preparation according to the above (14), wherein a base material of the sustained-release preparation is a material derived from a living body or a synthetic polymer;
(16) The sustained-release preparation according to the above (15), wherein the material derived from a living body or a synthetic polymer is a biodegradable polymer;
(17) A sustained-release preparation which comprises lactic acid/glycolic acid copolymer having the molar ratio of the lactic acid/glycolic acid of 60/40 to 70/30 and a growth hormone;
(18) A process for producing a sustained-release preparation which comprises using the finely divided protein powder obtained by the process according to the above (12);
(19) Use of the finely divided protein powder according to the above (7) for manufacturing a sustained-release preparation;
(20) The process according to the above (1), wherein the protein-containing solution is not frozen by spraying;
(21) The process according to the above (1), wherein the protein-containing solution is applied or dropped at a rate of about 10 to 250 mL/5 min. per 1300 cm$^2$ of the refrigerant carrier cooled to about −25° C. or lower before application or drop;
(22) The process according to the above (1), wherein drying is carried out under reduced pressure; and
(23) The process according to the above (1), wherein freezing is carried out by using a shelf of a freeze-dryer.

BEST MODE OF CARRYING OUT THE INVENTION

Figure 1:
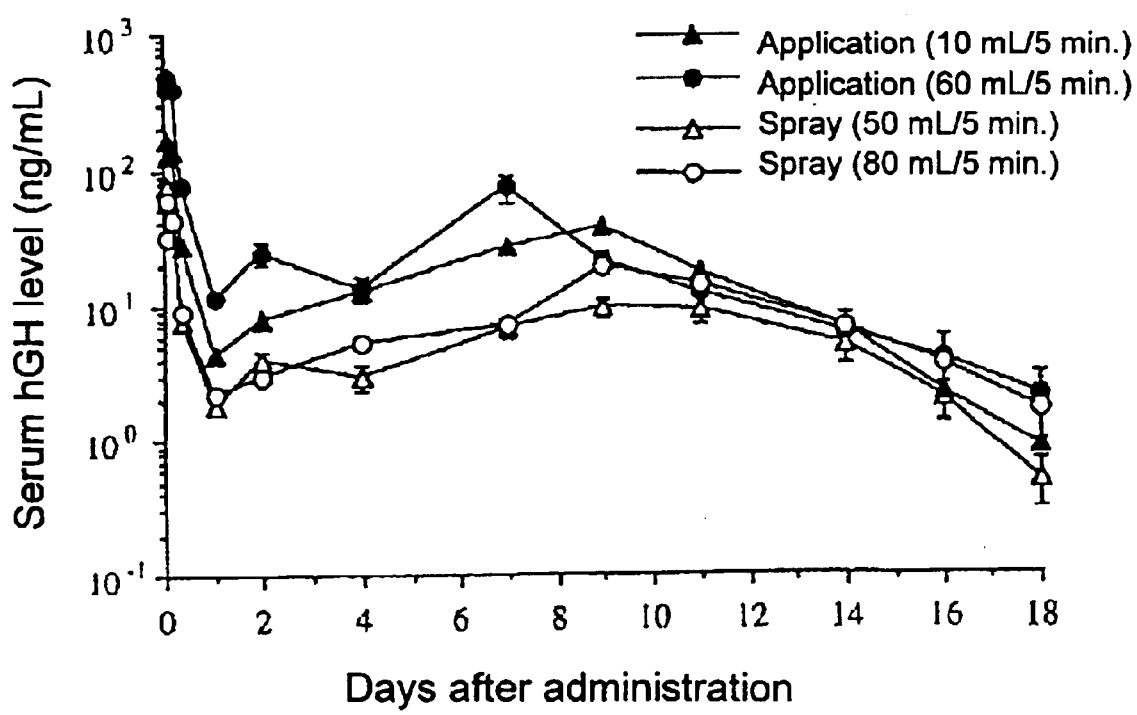
FIG. 1 is a graph which shows the change of hGH serum level after administration of microcapsules prepared using hGH powders to the immune suppressed SD rats, wherein hGH powders are obtained by freezing the hGH-containing solution by means of application [amount of application: 10 mL/5 min. (-▲-), 60 mL/5 min. (- -)] and spraying [amount of spraying: 50 mL/5 min. (-△-), 80 mL/5 min. (-○-)], respectively.

The proteins to be used in the present invention may be any proteins such as natural products, synthetic products, semi-synthetic products and those produced by gene recombinant technology, and the like. Further, their derivatives, analogues and muteins may be included. In general, for obtaining a large amount of a protein having high purity, gene recombinant technology is often employed.

Examples of the proteins to be used in the present invention include those having a molecular weight of, preferably about 5,000 to 1,000,000 dalton, more preferably of about 6,000 to about 200,000 dalton.

Specific examples of the proteins to be used in the present invention include hormones, cytokines, hematopoietic factors, growth factors, and the like.

The hormones described above may be those having any of agonistic and antagonistic functions. Examples of the hormones include insulin, growth hormones (GH), prolactin, thyroid-stimulating hormone (TSH), luteinizing hormone (LH), follicle-stimulating hormone (FSH), human chorionic gonadotropin (HCG), thymosin, parathyroid hormone (PTH), etc. The hormones are preferably insulin and growth hormones, more preferably growth hormones.

Examples of the growth hormones may be those derived from any species, preferably those derived from human beings. Although the growth hormones to be used in the present invention may be those derived from natural sources such as a growth hormone extracted from anterior pituitary, etc., they are preferably gene recombinant type GH (JP-B 6-12996, JP-B 6-48987), more preferably recombinant type hGH having the same structure as that of a naturally occurring type which does not contain methionine at the N-terminus. Such hGH having the same structure as that of a naturally occurring type which does not contain methionine at the N-terminus can be obtained according to a process described in JP-A 10-72489 (EP-A 812856) or WO 00/20439. The GH may be a metal salt (including metal complex; metal being zinc, etc.) and GH which is substantially free from a metal may also be used. As hGH, not only that having a molecular weight of about 22 k dalton but also that having a molecular weight of about 20 k dalton (JP-A 7-101877, JP-A 10-265404) may be used. In addition, as hGH, a derivative of hGH or its related protein (WO 99/03887) may also be used.

The cytokines include, for example, lymphokines and monokines, etc. Examples of the lymphokines include interferons (alpha, beta and gamma) and interleukins (IL-2, 3, 4, 5, 6, 7, 8, 9, 10, 11, 12), etc. Examples of the monokines include interleukin-1 (IL-1), tumor necrosis factor (TNF), etc. The preferred cytokine is a lymphokine, etc., more preferred interferon, etc., particularly preferred one is interferon-α.

Examples of the hematopoietic factors include erythropoietin (EPO), colony stimulating factors (G-CSF, GM-CSF, M-CSF, etc.), thrombopoietin (TPO), platelet-derived growth factor, megakaryocyte potentiator, etc.

Examples of the growth factors include basic and acidic fibroblast growth factors (FGF) and their families (e.g., EGF, TGF-α, TGF-β, PDGF, acidic FGF, basic FGF, FGF-9, etc.), hepatic cell growth factor (HGF), vascular endothelial cell growth factor (VEGF), nerve growth factor (NGF) and its family (e.g., BDNF, NT-3, NT-4, CNTF, GDNF, etc.), insulin-like growth factors (e.g. IGF-1, IGF-2, etc.) and bone morphogenetic protein (BMP) and its family, etc.

Examples of the enzymes include superoxide dismutase (SOD), urokinase, tissue plasminogen activator (TPA), asparaginase, kallikrein, etc.

In addition, the proteins to be used in the present invention include thymopoietin, blood thymic factor (FTS) and derivatives thereof (U.S. Pat. No. 4,229,438), other thymic factors [Igaku no Ayumi, Vol. 125, No. 10, pp. 835–843 (1983)], and the like.

The proteins to be used in the present invention are preferably hormones, more preferably growth hormones and insulin, and particularly preferred is human growth hormone.

In the present invention, the protein may contain a metal. When the protein contains a metal, the content of the metal is preferably not greater than 0.1% (w/w), more preferably not greater than 0.01% (w/w), and most preferably not greater than 0.001% (w/w). Thus, substantially metal-free physiologically active polypeptides are most suited for the present invention. Crystalline insulin, for example, usually contains small amounts of heavymetals such as zinc, nickel, cobalt and cadmium, etc. Insulin containing 0.4% (w/w) zinc exists as a stable hexamer and appears to be relatively inert in the interaction with the metal salt of biodegradable polymer.

If necessary, the metal occurring in the protein can be previously removed. As the method of removing the metal for the protein, known methods are employed. For example, dialyzing an acidic aqueous hydrochloric acid solution of insulin against water or an aqueous solution of ammonium acetate and lyophilizing the dialysate can provide amorphous insulin with minimal metal content.

When it is need that the desired protein is purged or purified from tissues, body fluids, chemically synthetic crude preparations, or recombinant cells or recombinant fungi, a standard isolation or purification method of proteins can be adopted ("Protein" written by Kazuo SATAKE published by Asakura Shoten; "Physiologically Active Peptide", Pharmacia Review, No. 3, published by the Pharmaceutical Society of Japan). In particular, by combining some liquid chromatographies ("High-speed Liquid Chromatography of Protein or Peptide" edited by Nobuo UI et al. published by Kagakudojin), it is possible to obtain the protein having high purity in high yield without loss of the physiologic activity. If necessary, the step of desalting can be preferably adopted as the final step of the process for purification.

The solvent of the protein-containing solution of the present invention is not specifically limited in so far as it can dissolve the protein. Preferably, the solvent is that having a freezing point of −130° C. or higher. Specific examples thereof include water, alcohols (e.g., methanol, ethanol, isopropanol, etc.), acetone, a mixed solvent of water and the above alcohols, a mixed solvent of water and an organic solvents suchas acetone, etc., and the like. Preferably, water is used. An organic solvent such as alcohols, acetone, etc., can be used as a "water-miscible organic solvent" described hereinafter.

Preferably, a volatile salt or a water-miscible organic solvent is added to the protein-containing solution using the above solvent. By lyophilizing the protein-containing solution obtained by adding a volatile salt or a water-miscible organic solvent, it is possible to prepare a protein powder which is easy of handling (superior for deal) and is very fine (has a smaller particle size).

As the volatile salt, which can be added to the protein-containing solution is, for example, ammonium salts (e.g., ammonium acetate, ammonium bicarbonate, ammonium carbonate, ammonium chloride, etc., preferably ammonium acetate, etc.). The volatile salt can be used in admixture thereof in an appropriate ratio. The added amount of the volatile salt relative to the protein-containing solution is, for example, about once to about 80 times mole (specifically, about 10 times to about 80 times mole), preferably about 10 times to about 70 times mole, more preferably about 15 times to about 70 times mole, further more preferably about 15 times to about 50 times mole, the most preferably about 15 times to about 40 times mole by mole ratio.

Examples of the water-miscible organic solvent, which can be added to the protein-containing solution include the above alcohols, acetone, etc. The above organic solvent can be used in admixture thereof having a suitable mixing ratio. A preferred organic solvent is alcohols, more preferable one is ethanol, alone. The added amount (concentration) of the water-miscible organic, is about 0.03 to 0.5% (V/V), preferably about 0.06 to 0.25% (V/V), more preferably about 0.1 to 0.15% (V/V), by volume ratio.

The water-miscible organic solvent and/or the volatile salt added to the protein-containing solution can be used alone or in admixture thereof. When the water-miscible organic solvent and the volatile salt are used in admixture thereof, they can be added into the protein-containing solution in accordance with the above amount respectively.

Preferably, the volatile salt is added to the protein-containing solution. More preferably, an ammonium salt is added and further more preferably, ammonium acetate is added.

The concentration of the protein-containing solution to be subjected to freezing is, for example, 0.01% (W/V) to 30% (W/V), preferably 0.03% (W/V) to 10% (W/V), more preferably 0.05% (W/V) to 3% (W/V), etc., however it is not particularly limited thereto. When the protein is hGH, the concentration of hGH in the protein-containing solution is preferably about 0.01% (W/V) to about 5% (W/V), more preferably about 0.05% (W/V) to about 2% (W/V), further more preferably about 0.05% (W/V) to about 0.5% (W/V).

The protein in the protein-containing solution to be subjected to freezing is preferably a single protein.

A freezing and drying method of the protein-containing solution in the present invention is not specifically limited. However, drying under reduced pressure (e.g., vacuum drying) is preferred. For example, freeze-dryer may be carried out in continuous steps by using a freeze-dryer (lyophilizer) or the protein-containing solution which has been frozen separately without using a freeze-dryer may be dried by a freeze-dryer.

An apparatus to be used for freezing is not specifically limited. However, it is preferred to use a shelf of a freeze-dryer which is normally used for lyophilization of injectable preparations of medicaments (freeze-dryer shelf) from the viewpoint of the economical, simple and convenient production of a protein powder. Detailed introduction of such a freeze-dryer is described in Masakazu KOBAYASHI, "Drug Production and Freeze-Dryer Technique" (Seizai to Kikai, Nos. 17–23, 25–35 and 38–46). According to these literatures, a temperature can be lowered to −70° C. by using a freeze-dryer shelf cooling with normal brine. Examples of these freeze-dryers include those manufactured by Kyowa Shinkuu Gijyutsu K. K. (e.g., RL series, RLC series, RLE series, R2L series, R2LW series or Triomaster series), those manufactured by Nippon Shinkuu Gijyutsu K.K. (e.g., DF series, DFM series) and the like. Further, since pre-freezers of these freeze-dryers are originally designed in such a way that materials can be dealt with under aseptic and dust-free conditions to adopt the dryers in the production of injectable preparations, the freeze-dryers are suitable for the production of a protein powder. Where liquefied gas is used as a primary refrigerant of a freeze-dryer and is introduced through a secondary refrigerant, it is also possible to further lower the temperature of a freeze-dryer shelf lower than that achieved by normal brine. For example, where liquid nitrogen is used as a primary refrigerant and is cooled via hydrofluoroether (HFE: manufactured by 3M), it is possible to lower the temperature to −135° C. in case of using HFE-7100 (manufactured by 3M) and to −117° C. in case of using HFE-72100 (manufactured by 3M), respectively. By using such a method, the protein-containing solution can be prevented from direct contact with liquefied gas and such a difficult problem as the necessity of aseptic and dust-free treatment of liquefied gas can be avoided. The preferred shelf temperature is about −130 to −20° C., more preferably-about −100 to −30° C. and further more preferably about −80 to −40° C. Thus, by freezing the protein-containing solution with a freeze-dryer shelf, it is possible to transfer the frozen material in turn into a vacuum drying step quickly.

Preferably, freezing is carried out on a refrigerant carrier placed on a freeze-dryer shelf. The refrigerant carrier is not specifically limited. However, preferably, the refrigerant carrier is, for example, a plate, a tray, etc., which permits application or dropping of the protein-containing solution, preferably, a tray, etc. The above plate, tray, etc. are not limited to one having a flat surface and may have an uneven or curved surface. The above plate, tray, etc. may be made of any material in so far as they can withstand the cooling rate of the present invention. Preferably, a refrigerant carrier made of a metal (e.g., stainless, etc.) is used. Preferably, the temperature of the refrigerant carrier (e.g., tray) at the start of application or dropping is about −25° C. or lower (e.g., −25° C. to −100° C., specifically −25° C. to −50° C.). The protein-containing solution may be additionally applied or dropped on the already frozen solution. The surface temperature of the frozen protein-containing solution at the start of application or dropping is preferably about −25° C. or lower (e.g., −25° C. to −100° C., specifically−25° C. to −50° C.). The surface temperature of the refrigerant carrier and the frozen protein-containing solution can be measured, for example, by a temperature sensor [e.g., thermocouple (TYPE T: manufactured by Okazaki Seisakusyo)].

When the protein-containing solution frozen separately without using a freeze-dryer is dried with a freeze-dryer, drying can be carried out, for example, by transferring the frozen solution with maintaining its frozen state to a shelf of the freeze-dryer.

The cooling rate of the protein-containing solution in the present invention can be appropriately controlled according to a particular king of the protein-containing solution, its protein concentration, concentration of additives, etc. Normally, the cooling rate of the protein-containing solution in the present invention is about −300 to −10° C./min., preferably about −250 to −40° C./min., more preferably −210 to −40° C./min., in particular, −210 to −70° C./min. The cooling rate in the present invention can be calculated on the basis of the temperature of the protein-containing solution before application or dropping, the temperature of the protein-containing solution upon freezing after application or dropping, and time required until completion of freezing. The temperature of the protein-containing solution upon freezing after application or dropping can be measured with the same temperature sensor as that described above.

In order to obtain the above cooling rate, for example, the protein-containing solution can be applied or dropped at a rate of about 10 to 250 mL/5 min., preferably about 15 to 200 mL/5 min., more preferably about 20 to 175 mL/5 min. per 1300 cm$^2$ of the refrigerant carrier which has been cooled to about −25° C. or lower (preferably about −100 to −25° C., more preferably about −100 to −30° C., further more preferably about −80 to −40° C.) before application or dropping. The contact (application or dropping) rate of the protein-containing solution can be appropriately selected from such a range that the above cooling rate can be achieved. The application or dropping rate of the protein-containing solution may be appropriately changed during contacting. The temperature of a refrigerant during the application or dropping may be about −2° C. and so on.

In the present invention, the application means to contact the protein-containing solution with the refrigerant carrier in the form of a continuous fluid from an opening (e.g., a charge nozzle of the protein-containing solution) without formation of droplets.

In the present invention, the dropping means to contact the protein-containing solution with the refrigerant carrier as a discontinuous fluid in the form of droplets from an opening (e.g., a charge nozzle of the protein-containing solution).

When application or dropping, a total amount of the protein-containing solution to be frozen can be applied or dropped at once. However, preferably, the solution is divided into several portions and they are applied or dropped intermittently so that the temperature of an already frozen part lowers, thereby keeping the desired cooling rate. When the protein-containing solution is applied or dropped intermittently, preferably, respective application or dropping operations is carried out at a certain time interval so that the temperature of the refrigerant carrier or an already frozen part lowers to −25° C. or lower.

In the present invention, the dropping fluid means both above-described continuous fluid which is contacted without formation of droplets, and discontinuous fluid when dropping. When application or dropping of the protein-containing solution, the diameter of the dropping fluid (maximum length of the horizontal cross-section) is, for example, about 0.1 to 40 mm, preferably, about 0.2 to 40 mm, more preferably about 0.3 to 10 mm. Although the dropping fluid is preferably in a columnar shape when application of the protein-containing solution, it may have various shapes according to the shape of an opening such as a prism shape having a polygonal cross-section (e.g., triangular, square, pentagonal or hexagonal cross-section, etc.). When dropping the protein-containing solution, the diameter of the droplets is preferably about 0.1 to 10 mm, more preferably about 0.7 to 7 mm, further more preferably about 1 to 5 mm. When dropping the protein-containing solution, the diameter of the opening (e.g., charge nozzle) is preferably about 0.05 to 10 mm, more preferably about 0.1 to 5 mm. Further, when dropping the protein-containing solution, the weight of the droplets is preferably about 0.0005 to 500 mg, more preferably about 0.2 to 180 mg, further more preferably about 0.5 to 65 mg.

In the present invention, it is possible to form ice laying on the refrigerant carrier when application or dropping of the protein-containing solution.

Further, in the present invention, it is possible to freeze the protein-containing solution in a layered state. The layer is preferably about 0.5 to 100 mm in thickness, more preferably about 1 to 80 mm in thickness, further more preferably about 3 to 50 mm in thickness.

Preferably, the protein powder obtained by the process of the present invention is further subjected to atomization treatment to obtain a further finely divided particles. As atomization treatment, various atomization methods known in the production of pharmaceuticals can be used. Examples of atomization methods include dry atomization such as a jet mill method. Further, as wet atomization, for example, the protein powder is dispersed in its insoluble solvent, and the dispersion is treated with sonication (probe type or bath type) stirring type atomizer (Polytron (manufactured by Kinemachica), Minimixer, Fillmix (manufactured by Tokushukika), Cleamix (manufactured by M Tech)), etc., followed by removing the solvent. The protein powder obtained by the process of the present invention can also be atomized by stirring or shaking it lightly in an insoluble solvent of the protein powder (e.g., dichloromethane, etc.).

When the protein powder thus obtained is used for a sustained-release preparation, preferably, the protein powder is added to a base material (e.g., a biodegradable polymer solution) directly, followed by subjecting the mixture to atomization treatment with sonication, a stirring type atomizer, etc.

For example, when Polytron of about 9 mm rotational diameter (manufactured by Kinemachica) is used as a stirring type atomizer, preferably, atomization treatment is carried out at a number of revolution of, preferably about 500 to 40,000 rpm, more preferably about 1,000 to 35,000 rpm, further more preferably about 5,000 to 30,000 rpm. At this time, stirring is carried out for, preferably about 5 seconds to 30 minutes, more preferably about 10 seconds to 20 minutes, further more preferably, about 15 seconds to 10 minutes. For example, when Polytron of about 9 mm rotational diameter (manufactured by Kinemachica) is used as a stirring type atomizer, atomization treatment is carried out, preferably, at about 500 to 40,000 rpm for about 5 seconds t 30 minutes, more preferably at about 1,000 to 35,000 rpm for about 10 seconds to 20 minutes, further more preferably at about 5,000 to 30,000 rpm for about 15 seconds to 10 minutes.

Although the average particle size of the finely divided protein powder after atomization treatment varies according to a particular drug delivery system to which the powder is applied, in general, the average particle size is preferably about 0.5 to 20 $\mu$m, more preferably about 0.7 to 10 $\mu$m, further more preferably about 1 to 5 $\mu$m. The average particle size of the finely divided protein powder of the present invention can be determined by a laser diffraction type particle size distribution analyzer (SALD 2000A: manufactured by Shimadzu). In the above determination, the finely divided protein powder is dispersed in an insoluble solvent of the powder (e.g., dichloromethane, etc.), followed by appropriate dilution to a measurable range by the above particle size distribution analyzer with the same solvent to determine the average particle size.

The protein powder and the finely divided protein powder produced by the present invention retain the higher-order structure of the protein in a high ratio even in comparison with that of the protein in the protein-containing solution (e.g., aqueous protein-containing solution) before subjecting it to the process of the present invention.

It is possible to confirm the secondary structure of the protein in the protein powder and the finely divided protein powder with FT-IR spectral analysis. This analysis is detailed in a review by Carpenter et al. (European Journal of Pharmaceutics and Biopharmaceutics, Vol. 45, pp 231–238, 1998), According to this review, it is reported that a content of $\alpha$-helix, which is one of secondary structures, in a protein powder and a finely divided protein powder obtained by lyophilization is lowered to less than that of an aqueous solution of the protein and, as a denaturation degree is higher, the lowering ratio of an $\alpha$-helix content is higher. Then, a degree of denaturation of a higher-order structure can be defined by a ratio of an $\alpha$-helix content of the protein powder or the finely divided protein powder obtained by the process of the present invention, which is determined by FT-IR spectral analysis, to an $\alpha$-helix content of the protein in the protein-containing solution (e.g., aqueous protein-containing solution) before subjecting to the process of the present invention.

When the denaturation degree of a protein is defined as described above, the protein powder and the finely divide protein powder obtained by the present invention retain preferably about 45% or more, more preferably about 50% or more of α-helix.

The protein powder and the finely divided protein powder retaining the higher-order structure (specifically, secondary structure, more specifically α-helix) obtained by the present invention can be used for various drug delivery systems. Examples of their administration routes include administration through lung, administration through mucosa (eyes, oral cavity, nose, uterus, vagina, rectum), oral administration, intracutaneous intramuscular or subcutaneous injection or implantation, injection or implantation in organs, etc., and the like. The protein powder and the finely divided protein powder can be administered in the form of a powder per se. Alternatively, they can be administered by formulating them in various pharmaceutical preparations (e.g., tablets, granules, sustained-release preparations, etc.), preferably sustained-release preparations. The sustained-release preparations can be prepared by compression method, spray-chilling method, spray-drying method, emulsifying method, phase separation method (Coacervation method), in-water drying method (S/O/W method), or the like using the protein powder or the finely divided protein powder and various base materials described hereinafter.

The base materials to be used for preparing the above sustained-release preparation may be any base materials derived from living bodies or those obtained by synthesis (e.g., synthetic polymers). In many cases, synthetic polymers are used.

Examples of the base materials derived from living bodies includegelatin, collagen, fats and oils (lipids, triglycerides, etc.), proteins derived from serum (albumin, globulin, etc.), keratin, chitin, chitosan, pullulan, celluloses (hydroxymethyl cellulose, carboxymethylcellulose, etc.) and the like.

As synthetic polymers, any of biodegradable polymers and non-biodegradable polymers may be used. However, biodegradable polymers are preferably used.

Examples of biodegradable polymers include polymers synthesized from one or more α-hydroxycarboxylic acids (e.g., glycolic acid, lactic acid, etc.), hydroxydicarboxylic acids (e.g., malic acid, etc.), hydroxytricarboxylic acids (e.g., citric acid, etc.) etc., by catalyst-free dehydration condensation polymerization and having a free carboxyl group(s) , mixtures thereof, poly-α-cyanoacrylic esters, polyamino acids (e.g., poly-γ-benzyl-L-glutamic acid, etc.) and maleic anhydride copolymers (e.g., styrene/maleic acid copolymers, etc.). The polymers may be homopolymers or copolymers. Polymerization may be of the random, block or graft type. When the above-mentioned α-hydroxycarboxylic acids, hydroxydicarboxylic acids and hydroxytricarboxylic acids have an optical active center in their molecular structures, they may be of the D-, L- or DL-configuration.

Among these polymers, a biodegradable polymer having a free terminal carboxyl group such as polymers synthesized from α-hydroxycarboxylic acids (e.g., glycolic acid, lactic acid, etc.) (e.g., lactic acid/glycolic acid copolymer, polylactic acid, etc.) and poly-α-cyanoacrylic acid esters are preferred. The biodegradable polymer is more preferably a polymer synthesized from α-hydroxycarboxylic acids, etc., especially preferably lactic acid/glycolic acid copolymer, etc. In the present specification, lactic acid/glycolic acid copolymer as well as homopolymers such as polylactic acid and polyglycolic acid is sometimes simply referred to as lactic acid/glycolic acid polymer.

When the biodegradable polymer used is a lactic acid/glycolic acid polymer (a lactic acid/glycolic acid copolymer or homopolymer), its composition ratio (mol %) is preferably about 100/0 to about 40/60, more preferably about 85/15 to about 50/50.

The weight-average molecular weight of the above-described lactic acid/glycolic acid polymer is preferably about 3,000 to about 50,000, more preferably about 3,000 to about 25,000, further more preferably about 5,000 to about 20,000.

The degree of dispersion (weight-average molecular weight/number-average molecular weight) of the lactic acid/glycolic acid polymer is preferably about 1.2 to about 4.0, more preferably about 1.5 to about 3.5.

Regarding weight-average molecular weight and degree of dispersion, the present specification holds that the former is in terms of polystyrene as determined by gel permeation chromatography (GPC) using 9 polystyrenes as reference substances with weight-average molecular weights of 120, 000, 52,000, 22,000, 9,200, 5,050, 2,950, 1,050, 580 and 162, respectively, and that the latter is calculated therefrom. The above determination is carried out using a GPC column KF804Lx 2 (produced by Showa Denko, Japan) and an RI monitor L-3300 (produced by Hitachi, Ltd., Japan) with chloroform as a mobile phase.

A biodegradable polymer having a free terminal carboxyl group(s) is a biodegradable polymer wherein the number-average molecular weight based on GPC measurement and the number-average molecular weight based on terminal group quantitation almost agree with each other. The number-average molecular weight based on terminal group quantitation is calculated as follows:

About 1 to 3 g of the biodegradable polymer is dissolved in a mixed solvent of acetone (25 ml) and methanol (5 ml), and the solution is quickly titrated with a 0.05 N alcoholic solution of potassium hydroxide while stirring at room temperature (20° C.) with phenolphthalein as an indicator to determine the carboxyl group content; the number-average molecular weight based on terminal group quantitation is calculated from the following equation:

Number-average molecular weight based on terminal group quantitation=20000×A/B

A: Weight mass (g) of biodegradable polymer

B: Amount (ml) of the 0.05 N alcoholic solution of potassium hydroxide added until titration end point is reached While the number-average molecular weight based on terminal group quantitation is an absolute value, that based on GPC measurement is a relative value that varies depending on various analytical conditions (e.g., kind of mobile phase, kind of column, reference substance, slice width chosen, baseline chosen etc.); it is therefore difficult to have an absolute numerical representation of these two values. However, the description that the number-average molecular weight based on GPC measurement and that based on terminal group quantitation almost agree means, for example, that the number-average molecular weight based on terminal group quantitation falls within the range from about 0.5 to about 2 times, preferably from about 0.7 to about 1.5 times, of the number-average molecular weight based on GPC measurement in a polymer which is synthesized from one or more α-hydroxycarboxylic acids.

For example, in the case of a polymer having a free terminal carboxyl group(s) and which is synthesized from one or more α-hydroxycarboxylic acids by catalyst-free dehydration condensation polymerization, the number-average molecular weight based on GPC measurement and the number-average molecular weight based on terminal group quantitation almost agree with each other. On the other hand, in the case of a polymer having substantially no free terminal carboxyl groups and which is synthesized from a cyclic dimer by ring-opening polymerization using a catalyst, the number-average molecular weight based on terminal group quantitation is significantly (about 2 times or more) higher than that based on GPC measurement. This difference makes it possible to clearly differentiate a polymer having a free terminal carboxyl group(s) from a polymer having no free terminal carboxyl group.

A lactic acid/glycolic acid polymer having a free terminal carboxyl group(s) can be produced by a per se known process such as that described in JP-A 61-28521 (e.g., process by catalyst-free dehydration condensation polymerization reaction or dehydration condensation polymerization reaction in the presence of an inorganic solid acid catalyst).

The decomposition/elimination rate of a lactic acid/glycolic acid polymer varies widely, depending on composition rate or weight-average molecular weight. A physiologically active polypeptide release duration can be extended (e.g., to about 6 months) by lowering the glycolic acid ratio or increasing the molecular weight, since decomposition/elimination is usually delayed as the glycolic acid ratio decreases. Conversely, drug release duration can be shortened (e.g., to about one week) by increasing the glycolic acid ratio or decreasing the molecular weight. To obtain a sustained-release preparation which can effectively release a physiologically active polypeptide for a period ranging from one week to two months, it is preferable to use a lactic acid/glycolic acid polymer whose composition ratio and weight-average molecular weight are within the above-described ranges.

Therefore, composition of a biodegradable polymer used in the present invention is preferably selected according to the desired kinds of a physiologically active polypeptide and the desired duration. In a specific example, for example, when GH is used as a physiologically active polypeptide, the biodegradable polymer is preferably lactic acid/glycolic acid polymer, more preferably lactic acid/glycolic acid copolymer. In the lactic acid/glycolic acid copolymer, lactic acid/glycolic acid composition ratio (mol %) is preferably about 85/15 to about 50/50, more preferably about 75/25 to about 50/50. The weight-average molecular weight of the lactic acid/glycolic acid copolymer is preferably about 8,000 to about 20,000, more preferably about 10,000 to about 20,000. Further, the degree of dispersion (weight-average molecular weight/number-average molecular weight) of the lactic acid/glycolic acid polymer is about 1.2 to about 4.0, more preferably about 1.5 to about 3.5.

The lactic acid/glycolic acid polymer used can be produced by the known methods such as those described in the above publication and the like. The polymer is preferably one that is produced by catalyst-free dehydration condensation polymerization. It is preferable that the lactic acid/glycolic acid polymer (PLGA) wherein the number-average molecular weight based on terminal group quantitation and the number-average molecular weight based on GPC measurement almost agree with each other is used.

Further, two kinds of lactic acid/glycolic acid polymers differing in composition ratio and/or weight-average molecular weight may be used in an admixture of given ratio. The typical example is a mixture of lactic acid/glycolic acid polymer wherein the composition ratio of lactic acid/glycolic acid (mol %) is about 75/25 and the weight-average molecular weight is about 10,000 and lactic acid/glycolic acid copolymer wherein the composition ratio of lactic acid/glycolic acid (mol %) is about 50/50 and the weight-average molecular weight is about 12,000. The preferred weight ratio of these copolymers of the mixture is about 25/75 to about 75/25, respectively.

The biodegradable polymer used in the present invention can be metal salts of the above mentioned biodegradable polymer. For example, various polyvalent metal salts of the biodegradable polymer and the like described in WO97/01331 can be used. Preferably, polyvalent metal salt of the lactic acid/glycolic acid polymer, etc., (more preferably, zinc salt, calcium salt, magnesium salt, etc., further more preferably zinc salt, etc.) can be used. The metal of the polyvalent metal salt used in this invention is not particularly limited as long as it dose not cause any adverse effect to a living body. It is exemplified by the polyvalent metal such as bivalent salts (e.g., Fe, Zn, Cu, Ca, Mg, Al, Sn, Mn, etc.), trivalent salts (e.g., Fe, Al, Mn, etc.), tetravalent salts (e.g., Sn, etc.) and the like.

In the present specification, the biodegradable polymer is sometimes referred as the biodegradable polymer also in case that it is the metal salt thereof. For example, also lactic acid/glycolic acid polymer is sometimes referred as lactic acid/glycolic acid polymer in case that it is the polyvalent metal salt thereof.

The above polyvalent metal salt of the biodegradable polymer can be produced by the method described in WO97/01331 or the other methods according to the method.

In case that polyvalent metal salt of the biodegradable polymer is the salt of zinc, it can also be produced by reaction of the biodegradable polymer and zinc oxide in an organic solvent. For example, zinc salt of the biodegradable polymer can be produced according to the following method.

First, an organic solvent solution of the biodegradable polymer-zinc oxide complex is prepared by coexistence of biodegradable polymer and zinc oxide in an organic solvent. In that case, although the concentration of the biodegradable polymer in the solvent is depending on molecular weight thereof or the kind of the organic solvent, etc., for example, the concentration is about 0.1 to about 80% (W/W), preferably about 1 to about 70% (W/W), more preferably about 2 to about 60% (W/W) Although the amount of the added zinc oxide is different depending on the kind of the organic solvent, for example, the amount is about 0.001 to about 2% (W/W), preferably about 0.01 to about 1.5% (W/W), more preferably about 0.1 to about 1% (W/W), based on the amount of the biodegradable polymer, as described in JP-A 10-231252. According the order to add the biodegradable polymer and zinc oxide into the organic solvent, zinc oxide in the condition of powder or suspended in the organic solvent can be added into the solution prepared by means of that the biodegradable polymer is dissolved into organic solvent, or on the contrary, the organic solvent solution of the biodegradable polymer can be added into the suspension prepared by means of that zinc oxide is suspended into the organic solvent. Both of the biodegradable polymer and zinc oxide can be mixed in the condition of powder, then the organic solvent can be added.

The organic solvent used for dissolving the biodegradable polymer in the production of the sustained-release preparation preferably has a boiling point not exceeding 120° C. Examples of the organic solvent include halogenated hydrocarbons (e.g., dichloromethane, chloroform, carbon tetrachloride, etc.), alcohols (e.g., ethanol, methanol, 1,4-butanediol, 1,5-pentanediol, etc.), ethyl acetate, acetonitrile, and so on. These solvents can also be used as a mixture in a given ratio. The preferred organic solvent used singly includes, for example, dichloromethane and acetonitrile, etc. The preferred organic solvent used as a mixture includes, for example, combination of halogenated hydrocarbons (e.g., dichloromethane, chloroform, etc.) and alcohols (e.g., ethanol, methanol, 1,4-butanediol, 1,5-pentanediol, etc.) or acetonitrile. Especially, combination of dichloromethane and acetonitrile is used widely. The mixing ratio (volume ratio) of halogenated hydrocarbons relative to alcohols or acetonitrile ranges from about 40:1 to about 1:1, preferably from about 20:1 to about 1:1. In particular, it is preferred that hydrocarbon halide (e.g., dichloromethane, etc.) is singly used, or the mix solvent consisted essentially of hydrocarbon halide and acetonitrile at mixing ratio of 9:1 to 1:1 is used. The concentration of the biodegradable polymer in the solution is different depending on molecular weight, the kind of the organic solvent and so on. For example, it can be about 0.01 to about 80% (W/W), preferably about 0.1 to about 70% (W/W), more preferably about 1 to about 60% (W/W).

The sustained-release preparation is produced by removing the organic solvent from the S/O dispersion wherein the protein powder (S phase) obtained by lyophilizing the protein-containing solution (e.g., physiologically active polypeptide solution), to which the water-miscible organic solvent and/or the volatile salt has been added, is dispersed into a solution of the living body-derived material or the synthetic polymer (e.g., biodegradable polymer) in an organic solvent (O phase). The production method is, for example, (a) in-water drying method (S/O/W method), (b) phase separation method (Coacervation method) and (c) spray-drying method, or other methods according to these methods. Hereinafter, there is described, for example, the method for producing the microcapsules, as the sustained-release preparation.

(a) In-water Drying Method (S/O/W Method)

According to this method, at first the water-miscible organic solvent and/or the volatile salt is added to the aqueous solution of the protein, and then, the protein powder (S phase) is produced by lyophilization. The biodegradable polymer is dissolved in the organic solvent, and then, the above protein powder is dispersed into the resulting organic solvent solution. The ratio (ratio by weight) of the protein and the biodegradable polymer is, for example, about 1:1000 to about 1:1, preferably about 1:200 to about 1:5, more preferably about 1:100 to about 1:5.

Preferably, an external physical energy is applied to disperse and atomize the protein powder uniformly in the organic solvent solution. For this, there can be used, for example, an irradiation of ultrasonic wave, a turbine stirrer, a homogenizer and so on. As to the average particle size of the protein in the organic solvent solution, it is preferably about 0.5 to 20 μm, more preferably about 0.7 to 10 μm, further more preferably about 1 to 5 μm, and which is easily realized by using the protein powder obtained by the process of the present invention.

Then, the organic solvent dispersion (S/O dispersion) thus prepared is further added to an aqueous solvent (W phase), and then the same external physical energy as above mentioned, for example, an irradiation of ultrasonic wave, a turbine stirrer, a homogenizer and so on is applied to form the S/O/W emulsion. Then, the organic solvent of O phase is evaporated to produce the microcapsules. The volume of the water phase is selected from the numbers generally about 1 times to about 10,000 times, preferably about 2 times to about 5,000 times, more preferably about 5 times to about 2,000 times based on the volume of the O phase.

An emulsifer may be added into the above external water phase. As the emulsifer, there may be used anyone which is capable of forming the generally stable S/O/W emulsion, to Examples of the above emulsifer include anionic surfactants, nonionic surfactants, derivatives of polyoxyethylene castor oil, polyvinylpyrrolidones, polyvinyl alcohols, carboxymethyl celluloses, lecithin, gelatin, hyaluronic acids, etc. These emulsifers may be used in admixture thereof in a given ratio. The concentration of the emulsifer(s) in the external water phase is, preferably about 0.001% to 20% (w/w), more preferably about 0.01% to 10% (w/w), particularly preferably about 0.05% to 5% (w/w).

The thus obtained microcapsules are recovered by centrifugation or filtration, washed with distilled water to remove the emulsifier(s), etc. adhering to the surface of microcapsules, re-dispersed in distilled water, and lyophilized. Then, if necessary, water and the organic solvent in the microcapsules are further removed by warming. The warming can be conducted under reduced pressure. Regarding the warming conditions, heating and drying are conducted at a temperature not lower than a glass transition temperature of the biodegradable polymer and not so high as to cause aggregation of respective microcapsule particles. The heating and drying are conducted preferably at a temperature ranging from 10° C. lower than the glass transition temperature of the biodegradable polymer to a temperature which is about 20° C. higher than the glass transition temperature. The glass transition temperature is defined as the intermediate glass transition point obtained using a differential scanning calorimeter when the temperature is increased at a rate of 10 to 20° C. per minute.

(b) Phase Separation Method (Coacervation Method)

When microcapsules are produced by this method, a coacervating agent is gradually added to the S/O dispersion described as the above (a) under stirring to precipitate and solidify microcapsules. The amount of the coacervating agent used is about 0.01 to about 1,000 times by volume, preferably about 0.05 to about 500 times by volume, especially preferably about 0.1 to about 200 times by volume. Any coacervating agent can be used, as long as it is a polymeric, mineral oil or vegetable oil compound miscible with the organic solvent for dissolution of a biodegradable polymer and it does not dissolve the biodegradable polymer used. Specifically, examples of such coacervating agents include silicone oil, sesame oil, soybeanoil, cornoil, cottonseedoil, coconutoil, linseedoil, mineral oil, n-hexane and n-heptane, etc. Two or more of these can be used in combination. The thus obtained microcapsules are recovered by filtration, washed repeatedly with heptane, etc. to remove the coacervating agent. Further, washing is conducted in the same manner as in the above (a), followed by lyophilization.

In the production of microcapsules by the in-water drying method or coacervation method, an antiaggregation agent can be added for preventing aggregation of particles. Examples of the antiaggregation agent can be used, for example, water-soluble polysaccharides such as mannitol, lactose, glucose, starches (e.g., corn starch, etc.), hyaluronic acid and its alakaline metal salt; protein such as glycine, fibrin and collagen; and inorganic salts such as sodium chloride and sodium hydrogen phosphate, etc.

(c) Spray-drying Method

When microcapsules are produced by the present method, the S/O dispersion described as above (a) is sprayed viaa nozzle into the drying chamber of a spray drier to volatilize the organic solvent in the fine droplets in a very short time to produce microcapsules. Such a nozzle include, for example, a two-fluid nozzle type, a pressure nozzle type and a rotary disc type, etc. It is also advantageous, if necessary, to spray an aqueous solution of the above-described antiaggregation agent via another nozzle in order to prevent aggregation of each microcapsules particle. The thus obtained microcapsules are washed in the same manner as in the above (a), if necessary followed by heating (if necessary under reduced pressure) to remove water and the organic solvent.

The sustained-release preparation in the present invention is preferably in the condition of finely divided particles (microparticles). Because, the sustained-release preparation is applied through the needle for injection which is generally used for subcutaneous injection or intramuscular injection, for fear the patient should feel excessive pain. The particle size of the sustained-release preparation is, for example, about 0.1 to 300 μm, preferably about 1 to 150 μm, more preferably about 2 to 100 μm as the average particle size.

The amount of the protein included in the sustained-release preparation is, for example, about 0.1 to 40% (W/W), preferably about 0.2 to 20% (W/W). The average particle size of the protein is preferably not more than about 0.5 to 20 μm, more preferably about 0.7 to 10 μm, further more preferably about 1 to 5 μm.

The amount of the living body-derived polymer or the synthetic polymer included in the sustained-release preparation is, for example, about 30 to 99.9% (W/W), preferably about 60 to 97% (W/W), more preferably about 70 to 90% (W/W).

The initial release ratio of the protein from the sustained-release preparation [the initial release ratio for one day (24 hours) after administration] is preferably not more than about 50%, more preferably about 1 to 40%, further more preferably about 3 to 35%. The initial release ratio can be calculated by an initial release amount for the first 24 hours after subcutaneous administration. The initial release amount can be obtained from measuring AUC (Area Under the Concentration) of the blood concentration for 24 hours after subcutaneous administration of the sustained-release preparation; and applying the AUC value to standard calibration curve of the dose-AUC, which curve is obtained by subcutaneous administration of the protein-containing solution.

For example, the sustained-release preparation can be used in the form of microcapsules, or can be used for preparing in various dosage forms using the microcapsules as a source material, and is capable of administering as parenteral preparations (e.g., injectable preparations or implantation in muscle, hypodermis, organs, etc., preparations for administering to mucosa onto cavitas nasi, rectum, uterus, etc.), oral preparations (solid preparations such as capsules (e.g., hard capsules, soft capsules, etc.), granules, powders, etc., liquid preparations such as suspensions, etc.) and so on.

In particular, the sustained-release preparation is preferably for injectable preparations. For example, in case that the sustained-release preparation is the microcapsules, it is possible to obtain the practical sustained-release preparation for injection by means of an aqueous suspension wherein the microcapsules are suspended together with dispersing agents (e.g., surfactants such as Tween 80, HCO-60, etc., polysaccharides such as carboxymethyl celluloses, sodium alginate, hyaluronic acid, etc.), preservatives (e.g., methylparaben, propylparaben, etc.), tonicity agents (e.g., sodium chloride, mannitol, sorbitol, glucose, etc.) and so on. It is also possible to obtain the practical sustained-release preparation for injection by means of an oily suspension wherein the microcapsules are suspended together with vegetable oil such as sesame oil, corn oil, a mixture thereof with a phospholipid such as lecithin, or medium-chain fatty acid triglycerides (e.g., Miglyol 812).

When the sustained-release preparation is, for example, microcapsules, the particle size of the sustained-release preparation for an injectable suspension can be selected from the range satisfying the requirements for the degree of dispersion and the needle passability for the injection. For example, the particle size is within the range of about 0.1 to about 300 μm, preferably about 1 to about 150 μm, more preferably about 2 to about 100 μm, as the average particle size.

Methods of preparing the above microcapsules as a sterile preparation include, but are not limited to, the method in which the entire production process is sterile, the method in which the gamma rays are used as the sterilant, and the method in which an antiseptic is added during the manufacturing process.

The sustained-release preparation can be safely used in mammals (e.g., humans, bovine, swine, dogs, cats, mice, rats, rabbits, etc.) with low toxicity.

Indication of the sustained-release preparation varies depending on the protein used. The sustained-release preparation is useful to prevent or treat diabetes when insulin is used as the protein; viral hepatitis (e.g., type C hepatitis, HBe antigen-positive active hepatitis, etc.) and cancer (e.g., renal carcinoma, multiple myeloma, etc.) when interferon-α is used; anemia (e.g., anemia during dialysis of kidney, etc.) when erythropoietin is used; neutropenia (e.g., in cancer therapy, etc.) and infections when G-CSF is used; cancer (e.g., hemangioendothelioma, etc.) when IL-2 is used; fracture, wound (e.g., bedsore, etc.), periodontitis and gastrointestinal ulcer when FGF is used; thrombocytopenia when FGF-9 is used; senile dementia and neuropathy when NGF is used; thrombosis when TPA is used; and cancer when tumor necrosis factor is used. Further, the sustained-release preparation containing GH is applied to treatment of Turner's syndrome, chronic renal diseases, achondroplasia, adult hypopituitarism and further decline such as adult growth hormone deficiency (adult GHD), AIDS, etc., in addition to pituitary dwarfism, based on growth hormone action of GH. Further, since, GH is reported to be applied to diseases such as Down syndrome, Silver syndrome, hypochondroplasia and juvenile chronic arthritis to provide excellent therapeutic effects, the sustained-release preparation containing GH can be applied to these diseases. The sustained-release preparation containing GH is also useful to prevent or treat congestive heart-failure, etc. In addition, the GH-containing sustained-release preparation can be applied to, for example, hematogenesis upon an organ transplant and chemotherapy of AIDS patients, improvement of nutrition, renal anemia, angina pectoris, hyperlipemia, obesity, acceleration of healing of burn, injury and ulcer, surgical invasion (operation, trauma)/early postoperative recovery, sepsis, prevention of fracture due to osteoporosis, early postoperative recovery of patients with fracture due to osteoporosis, amyotropic lateral sclerosis (ALS), bedscore, and the like. Further, the preparation is expected to be useful as an anti-senility agent for improving the quality of life (QOL) of weak old people, or is expected to inhibit the progress and improve neurodegenerative diseases (Alzheimer's disease, Perkinson's disease, cerebrovascular disease, etc.) by nerve protecting activity of hGH. In comparison with subcutaneous injection of GH every day, a better pharmacological activity against these diseases can be obtained by formulating GH in the form of the sustained-release preparation.

Although the dose of the sustained-release preparation varies depending on the kinds and contents of the protein, duration of the release, target disease, subject animal species and other factors, the dose can be set at any level, as long as the effective concentration of the protein in the body is maintained. For example, when the sustained-release preparation is one designed for two week release, the dose of the protein can be suitably chosen from the range of preferably about 0.0001 to about 10 mg/kg body weight, more preferably about 0.05 to about 1 mg/kg body weight, per an adult. When the sustained-release preparation is one designed for one month release, the dose of the protein can be suitable chosen from the range of preferably about 0.0002 to about 20 mg/kg body weight, more preferably about 0.1 to about 2 mg/kg body weight.

The preferred administration frequency of the sustained-release preparation can be suitably chosen from once a week, once every two weeks, once a month, once every two months and etc. depending on the kinds and contents of the protein, the dosage form, duration of the release, target disease, subject animal species and other factors. Preferably, the sustained-release preparation is one designed for one week release to two month release, more preferably from one week to one month release.

For example, in case of the sustained-release preparation which can effectively release the protein for a period of about two weeks, it is preferred to use lactic acid/glycolic acid polymer having a molar ratio of lactic acid/glycolic acid of 55:45 to 45:55 (e.g., about 50:50) as the base material of the sustained-release preparation. Further, preferably, the weight-average molecular weight of the lactic acid/glycolic acid polymer is about 10,000 to 15,000 (e.g., 13,000).

When the protein as an active ingredient in the sustained-release preparation is, for example, insulin, the dose per administration to an diabetic adult is suitably chosen from the range of usually about 0.001 to about 1 mg/kg body weight, preferably about 0.01 to about 0.2 mg/kg body weight, as an effective ingredient. And the preferred administration frequency is once a week.

When the protein as an active ingredient in the sustained-release preparation is GH, the dose can be set at any level, as long as the effective concentration of GH in the body is maintained, although varying depending on the kinds and contents of GH, duration of the release, target disease, subject animal species and other factors. Regarding the treatment of the above described diseases, when the sustained-release preparation is one designed for two week release, the dose of GH can be suitably chosen from the range of about 0.01 to about 5 mg/kg body weight (about 0.03 to about 15 IU/mg/kg body weight), more preferably about 0.05 to about 1 mg/kg body weight (about 0.15 to about 3 IU/mg/kg body weight), per a child or an adult for safe administration. The preferred administration frequency can be suitably chosen from once a week, once every two weeks, once a month and etc., depending on the contents of GH, the dosage form, duration of the release, target disease, subject animal species and other factors.

The sustained-release preparation is preferably stored at ordinary temperature or in cold place. More preferably, the sustained-release preparation is stored in cold place. The "ordinary temperature" and the "cold place" are defined in the pharmacopoeia of Japan. Namely, the "ordinary temperature" means 15 to 25° C., and the "cold place" means a temperature not exceeding 15° C. In the "cold place", it is more preferably about 2 to 8° C.

On the other hand, it is desired to provide a sustained-release preparation containing GH which can effectively release GH for a period of about three to five weeks. During bringing the present invention to completion, the present inventors have found that a sustained-release preparation containing GH which is designed for about 3 to 5 week release can be obtained by using a specific base material for a sustained-release preparation.

The sustained-release preparation containing GH which is designed for about 3 to 5 week release can be obtained, for example, according to the above process for producing microcapsules. A GH powder to be used for the production of microcapsules may be produced by any process including that of the present invention. The average particle size of GH powder is, preferably about 0.5 to 20 $\mu$m, more preferably about 0.7 to 10 $\mu$m, further more preferably about 1 to 5 $\mu$m. In addition, regarding the definition of the degree of denaturation of GH, the GH powder retains about 45% or more, preferably about 50% or more α-helix.

As the base material of the sustained-release preparation, it is preferred to use a lactic acid/glycolic acid polymer having a lactic acid/glycolic acid molar ratio of about 60:40 to 70:30 (e.g., about 65:35). Further, preferably, the weight-average molecular weight of the lactic acid/glycolic acid polymer is about 10,000 to 18,000 (e.g., 14,500).

When the GH-containing sustained-release microcapsules designed for about 3 to 5 week release thus obtained is used as a injectable preparation for treating the above-described diseases, the dose of GH as an active ingredient can be suitably chosen from the range of about 0.02 to about 10 mg/kg body weight (about 0.06 to about 30 IU/mg/kg body weight), more preferably about 0.1 to about 2 mg/kg body weight (about 0.15 to about 3 IU/mg/kg body weight), per a child or an adult for safe administration.

EXAMPLES

The present invention is hereinafter described in more detail by means of the following Examples, Comparative Examples, Reference Examples and Experimental Examples, and which are not to be construed to limit the scope of the present invention.

In the following Examples, when confirmation of freezing is difficult, for calculating a cooling rate, a temperature drop in arbitrary unit time (longer than 10 seconds) was calculated and the maximum value calculated was taken as the cooling rate.

Example 1

Freezing of Aqueous Bovine Serum Albumin (BSA) Solution and Subsequent Vacuum Drying Twenty-fold molar equivalent of ammonium acetate was added to an aqueous BSA solution (the final concentration of BAS=2 mg/mL) and the mixture was filtered through a 0.22 $\mu$m filter to prepare a solution formulation for freeze-drying (Formulation 1). After cooling the solution below 1° C., given amount portions thereof of about 0.3 to 0.5 mm fluid diameter were applied to a tray (area: about 1,300 cm$^2$) on a freeze-dryer shelf cooled at −45 to −40° C. every 5 minutes, and freeze-dried (Triomaster A04: Kyowa Vacuum (condensation capacity 10 kg type)) to prepare a BSA powder. The temperature of the tray during application was −40 to −30° C. In a solution (O) of 1.85 g of lactic acid/glycolic copolymer (PLGA) (lactic acid/glycolic acid (molar ratio) about 50/50, the weight average molecular weight converted to polystyrene=about 13,000) and 10 mg of zinc oxide in 2.7 mL of dichloromethane, 140 mg of the BSA (S) was treated with Polytron (manufactured by Kinemachica) to disperse and atomize the powder in the solution. After addition of 2.5 mL of dichloromethane to 100

μl of the resulting S/O dispersion, the average particle size of the finely divided BSA powder was measured by a laser diffraction particle size analyzer (SALD2000A manufactured by Shimadzu).

Table 1 shows the average particle size of the finely divided BSA powder obtained by freezing Formulation 1 according to the above process. The mean cooling rate of Formulation 1 became −108.7° C./min. (maximum −156° C./min.) to −35.1° C./min. (minimum −32.4° C./min.) by adjusting the amount of application to the tray to 10 mL/5 min. to 80 mL/5 min. Thus, it was possible to control the average particle size of the finely divided BSA powder to 1.2 μm to 6.1 μm.

TABLE 1

| | Application Amount (amount (mL) per 5 min./tray) | | | |
|---|---|---|---|---|
| | 10 | 25 | 40 | 50 |
| Average particle size (μm) | 1.2 | 2.8 | 3.1 | 2.5 |
| Mean cooling rate (° C./min.) | −108.7 | −92.1 | −66.0 | −68.8 |

| | Application Amount (amount (mL) per 5 min./tray) | | |
|---|---|---|---|
| | 60 | 70 | 80 |
| Average particle size (μm) | 3.5 | 4.2 | 6.1 |
| Mean cooling rate (° C./min.) | −58.3 | −49.4 | −35.1 |

Example 2

Freezing of Aqueous BSA Solution and Subsequent Vacuum Drying

According to the same manner as that described in Example 1, the aqueous BSA solution of Formulation 1 was prepared. The temperature of the solution was adjusted to room temperature and given amount portions thereof of about 0.3 to 0.5 mm fluid diameter were applied to a tray (area: about 1,300 cm²) on a freeze-dryer shelf cooled at −45 to −40° C. every 5 minutes, and freeze-dried (RL-603BS: Kyowa Vacuum (condensation capacity 60 kg type)) to prepare a BSA powder aseptically. The temperature of the tray during application was −40 to −30° C. By using the resulting BSA powder, the average particle size of the finely divided BSA powder was measured according to the same manner as that described in Example 1.

Table 2 shows the average particle size of the finely divided BSA powder obtained by freezing Formulation 1 according to the above process. The mean cooling rate of Formulation 1 became −98.9° C./min. (maximum −101.1° C./min.) to −80.6° C./min. (minimum −70.3° C./min.) by adjusting the amount of application to the tray to 30 mL/5 min. to 60 mL/5 min. Thus, it was possible to control the average particle size of the finely divided BSA powder to 1.2 μm to 5.0 μm.

TABLE 2

| | Application Amount (amount (mL) per 5 min./tray) | | | |
|---|---|---|---|---|
| | 30 | 40 | 50 | 60 |
| Average particle size (μm) | 1.2 | 1.9 | 2.4 | 5.0 |
| Mean cooling rate (° C./min.) | −98.9 | −97.7 | −95.4 | −80.6 |

Example 3

Freezing of Aqueous hGH Solution and Subsequent Vacuum Drying

Twenty-fold molar equivalent of ammonium acetate was added to an aqueous solution of gene recombinant type hGH (the final concentration of hGH=2 mg/mL) and the mixture was filtered through a 0.22 μm filter to prepare a solution formulation for freeze-drying (Formulation 2). After cooling the solution below 10° C., given amount portions thereof of about 0.3 to 0.5 mm fluid diameter were applied to a tray (area: about 1,300 cm²) on a freeze-dryer shelf cooled at −45 to −40° C. every 5 minutes, and freeze-dried (Triomaster A04: Kyowa Vacuum (condensation capacity 10 kg type)) to prepare a lyophilized powder (hereinafter abbreviated as hGH powder). The temperature of the tray during application was −40 to −30° C. By using the resulting hGH powder, the average particle size of the finely divided hGH powder was measured according to the same manner as that described in Example 1.

Table 3 shows the average particle size of the finely divided hGH powder obtained by freezing Formulation 2 according to the above process. The mean cooling rate of Formulation 2 became −201.0° C./min. (maximum −203.7° C./min.) to −72.5° C./min. (minimum −54.6° C./min.) by adjusting the amount of application to the tray to 10 mL/5 min. to 86 mL/5 min. Thus, it was possible to control the average particle size of the finely divided hGH powder to 1.4 μm to 4.7 μm.

TABLE 3

| | Application Amount (amount (mL) per 5 min./tray) | | | |
|---|---|---|---|---|
| | 10 | 60 | 70 | 86 |
| Average particle size (μm) | 1.4 | 2.3 | 3 | 4.7 |
| Mean cooling rate (° C./min.) | −201.0 | −88.7 | −84.1 | −72.5 |

Example 4

Freezing of Aqueous hGH Solution and Subsequent Vacuum Drying

Formulation 2 was prepared. The temperature was adjusted to room temperature, and given amount portions thereof of about 0.3 to 0.5 mm fluid diameter were applied to a tray (area: about 1,300 cm ) on a freeze-dryer shelf cooled at −45 to −40° C. every 5 minutes, and freeze-dried (RL-603BS: Kyowa Vacuum (condensation capacity 10 kg type)) to prepare hGR powder aseptically. The temperature of the tray during application was −40 to −30° C. By using the resulting hGH powder, the average particle size of the finely divided hGH powder was measured according to the same manner as that described in Example 1.

Table 4 shows the average particle size of the finely divided hGH powder obtained by freezing Formulation 2 according to the above process. The mean cooling rate of Formulation 2 became −84.6° C./min. (maximum −87.4° C./min.) to −67.3° C./min. (minimum −54.9° C./min.) by adjusting the amount of application to the tray to 50 mL/5 min. to 80 mL/5 min. Thus, it was possible to control the average particle size of the finely divided hGH powder to 2.7 μm to 5.5 μm.

TABLE 4

| | Application Amount (amount (mL) per 5 min./tray) | | | |
|---|---|---|---|---|
| | 50 | 60 | 70 | 80 |
| Average particle size (μm) | 2.7 | 2.7 | 3.2 | 5.5 |
| Mean cooling rate (° C./min.) | −84.6 | −80.6 | −76.6 | −67.3 |

Example 5A

Freezing of Aqueous BSA Solution and Subsequent Vacuum Drying

The aqueous BSA solution of Formulation 1 was prepared. The temperature of the solution was adjusted to room temperature and given amount portions in the form of droplets of about 2 to 3 mm fluid diameter were added dropwise to a tray (area: about 1,300 cm$^2$) on a freeze-dryer shelf cooled at −45 to −40° C. every 5 minutes, and freeze-dried (Triomaster A04: Kyowa Vacuum (condensation capacity 10 kg type)) to prepare a BSA powder. The temperature of the tray during dropwise-addition was −40 to −32° C. in case of a dropping rate per tray of 60 mL/5 min., −32 to −22° C. in case of a dropping rate per tray of 80 mL/5 min., −34 to −9° C. in case of a dropping rate per tray of 140 mL/5 min., −26 to −8° C. in case of a dropping rate per tray of 160 mL/5° C., and −22 to −4° C. in case of dropping rat per tray of 150 mL/5 min. By using the resulting BSA powder, the average particle size of the finely divided BSA powder was measured according to the same manner as that described in Example 1. When the dropping rate per tray was 150 mL/5 min., a silicone tube of 2 mm diameter of a charge nozzle was converted to that of 4 mm diameter.

Table 5 shows the average particle size of the finely divided BSA powder obtained by freezing Formulation 1 according to the above process. The mean cooling rate of Formulation 1 became −92.6° C./min. (maximum −101.1° C./min.) to −33.4° C./min. (minimum −32.6° C./min.) by adjusting the dropping rate to the tray to 60 mL/5 min. to 160 mL/5 min. Thus, it was possible to control the average particle size of the finely divided BSA powder to 1.3 μm to 20.0 μm.

TABLE 5

| | Dropping rate (amount (mL) per 5 min./tray) | | | | |
|---|---|---|---|---|---|
| | 50 | 80 | 140 | 160 | 150* |
| Average particle size (μm) | 1.3 | 1.4 | 2.4 | 3.8 | 20.0 |
| Mean cooling rate (° C./min.) | −92.6 | −85.3 | −71.7 | −49.7 | −33.4 |

*The tube was converted.

Example 5B

Freezing of Aqueous BSA Solution and Subsequent Vacuum Drying

The aqueous BSA solution of Formulation 1 was prepared. The temperature of the solution was adjusted to room temperature given amount portions thereof in the form of droplets of about 2 to 3 mm fluid diameter were added dropwise continuously to a tray (area: about 1,300 cm$^2$) on a freeze-dryer shelf cooled at −50 to −40° C., and freeze-dried (RL-402BS: Kyowa Vacuum (condensation capacity 40 kg type)) to prepare a BSA powder aseptically. The temperature of the tray during dropwise-addition of 500 mL of Formulation 1 was −40 to −31° C. in case of a dropping rate per tray of 60 mL/5 min., −38 to −30° C. in case of a dropping rate per tray of 80 mL/5 min., −28 to −12° C. in case of a dropping rate per tray of 120 mL/5 min.

In a solution (O) of 1.69 g of lactic acid/glycolic copolymer (PLGA) (lactic acid/glycolic acid (molar ratio)=about 65/35, the weight average molecular weight converted to polystyrene=about 14,500) and 10 mg of zinc oxide in 2.7 mL of dichloromethane, 300 mg of the resulting BSA (S) was treated with Polytron (manufactured by Kinemachica) to disperse and atomize the powder in the solution. After addition of 2.5 mL of dichloromethane to 100 μl of the resulting S/O dispersion, the average particle size of the finely divided BSA powder was measured by a laser diffraction particle size analyzer (SALD2000A manufactured by Shimadzu).

Table 6 shows the average particle size of the finely divided BSA powder obtained by freezing Formulation 1 according to the above process. The mean cooling rate of Formulation 1 became −93.7° C./min. (maximum −104.2° C./min.) to −59.8° C./min. (minimum −57.4° C./min.) by adjusting the dropping rate to the tray to 60 mL/5 min. to 120 mL/5 min. Thus, it was possible to control the average particle size of the finely divided BSA powder to 1.2 μm to 2.4 μm.

TABLE 6

| | Dropping rate (amount (mL) per 5 min./tray) | | |
|---|---|---|---|
| | 60 | 80 | 120 |
| Average particle size (μm) | 1.2 | 1.4 | 2.4 |
| Mean cooling rate (° C./min.) | −93.7 | −88.5 | −59.8 |

Example 6A

Freezing of Aqueous hGH Solution and Subsequent Vacuum Drying

Formulation 2 was prepared. The temperature was adjusted to room temperature, and given amount portions in the form of droplets of about 2 to 3 mm fluid diameter were added dropwise continuously to a tray (area: about 1,300 cm$^2$) on a freeze-dryer shelf cooled at −45 to −40° C., and freeze-dried (Triomaster A04: Kyowa Vacuum (condensation capacity 10 kg type)) to prepare hGH powder. The temperature of the tray during dropwise-addition was −38 to −18° C. in case of a dropping rate per tray of 140 mL/5 min., −28 to −2° C. in case of a dropping rate per tray of 160 mL/5 min. By using the resulting hGH powder, the average particle size of the finely divided hGH powder was measured according to the same manner as that described in Example 1.

Table 7 shows the average particle size of the finely divided hGH powder obtained by freezing Formulation 2 according to the above process. The mean cooling rate of Formulation 2 became −74.1° C./min. (maximum −79.2° C./min.) to −42.6° C./min. (minimum −39.8° C./min.) by adjusting the dropping rate to the tray to 140 mL/5 min. to 160 mL/5 min. Thus, it was possible to control the average particle size of the finely divided hGH powder to 1.9 μm to 5.9 μm.

TABLE 7

| | Dropping rate (amount (mL) per 5 min./tray) | |
|---|---|---|
| | 140 | 160 |
| Average particle size (μm) | 1.9 | 5.9 |
| Mean cooling rate (° C./min.) | −74.1 | −42.6 |

Example 6B

Freezing of Aqueous hGH Solution and Subsequent Vacuum Drying

Twenty-fold molar equivalent of ammonium acetate was added to an aqueous solution of hGH (the final concentration of hGH=5 mg/mL) and the mixture was filtered through a 0.22 μm filter to prepare a solution formulation for freeze-drying (Formulation 3) and the aqueous hGH solution of Formulation 2 was also prepared. Each Formulation was adjusted to room temperature and given amount portions thereof in the form of droplets of about 2 to 3 mm fluid diameter were added dropwise continuously to a tray (area: about 1,300 cm$^2$) on a freeze-dryer shelf cooled at −50 to −40° C., and freeze-dried (RL-402BS: Kyowa Vacuum (condensation capacity 40 kg type)) to prepare a hGH powder aseptically. The temperature of the tray during dropwise-addition was −35 to −25° C. in case of a dropping rate per tray of 60 mL/5 min. (amount of the solution to be contacted: 1 L), −31 to −24° C. in case of a dropping rate per tray of 80 mL/5 min. (amount of the solution to be contacted: 500 mL), about −30° C. in case of a dropping rate per tray of 94 mL/5 min (amount of the solution to be contacted: 250 mL). By using the resulting hGH powder, the average particle size of the finely divided hGH powder was measured according to the same manner as that described in Example 5B.

Table 8 shows the average particle size of the finely divided hGH powder obtained by freezing each of Formulations 2 and 3 according to the above process. When the mean cooling rate of Formulation 2 was −87.4° C./min. (maximum −95.3° C./min.) to −83.5° C./min. (minimum −76.6° C./min.), it was possible to control the average particle size of the finely divided hGH powder to 1.3 μm to 1.8 μm. In case of the finely divided hGH 5 powder of Formulation 3, when the mean cooling rate was −93.4° C./min., it was possible to control the average particle size of the finely divided hGH powder to 1.8 μm.

TABLE 8

| | Dropping rate (amount (mL) per 5 min./tray) | |
|---|---|---|
| | 94 (contact amount 250 mL) Formulation 2 | 60 (contact amount 1L) Formulation 2 |
| Average particle size (μm) | 1.3 | 1.8 |
| Mean cooling rate (° C./min.) | −87.4 | −86.4 |

TABLE 8-continued

| | Dropping rate (amount (mL) per 5 min./tray) | |
|---|---|---|
| | 80 (contact amount 500 mL) Formulation 2 | 80 (contact amount 100 mL) Formulation 3 |
| Average particle size (μm) | 1.8 | 1.8 |
| Mean cooling rate (° C./min.) | −83.5 | −93.4 |

Example 6C

Freezing of Aqueous hGR Solution and Subsequent Vacuum Drying

The aqueous hGH solution of Formulation 2 was prepared. The solution was adjusted to room temperature and given amount portions thereof in the form of droplets of about 2 to 3 mm fluid diameter were added dropwise continuously to a tray (area: about 1,300 cm$^2$) on a freeze-dryer shelf cooled at −50 to −40° C. to contact 1 L of the solution, and freeze-dried (RL-402BS: Kyowa Vacuum (condensation capacity 40 kg type)) to prepare a hGH powder aseptically.

By using the hGH powder obtained at the dropping rate per tray of 60 mL/5 min. or 80 mL/5 min., the average particle size of the finely divided hGH powder was measured according to the same manner as that described in Example 5B. Further, By using the hGH powder obtained at the dropping rate per tray of 120 mL/5 min. or 140 mL/5 min., the average particle size of the finely divided hGH powder prepared according to the same manner as that described in Example 1 was measured.

Table 9 shows the average particle size of the finely divided hGH powder obtained by freezing Formulation 2 according to the above process. When 1 L of the aqueous hGH solution was contacted, it was possible to control the average particle size of the finely divided hGH powder to 1.6 μm to 4.0 μm by controlling the dropping rate to 60 mL/5 min. to 140 mL/5 min.

TABLE 9

| | Dropping rate (amount (mL) per 5 min./tray) | |
|---|---|---|
| | 60 (contact amount 1L) | 80 (contact amount 1L) |
| Average particle size (μm) | 1.6 | 2.5 |
| | Dropping rate (amount (mL) per 5 min./tray) | |
| | 120 (contact amount 1L) | 140 (contact amount 1L) |
| Average particle size (μm) | 3.1 | 4.0 |

Reference Example 1

Freeze-vacuum Drying of Aqueous BSA Solution

The aqueous BSA solution of Formulation 1 was prepared. The solution was added to a tray so that a layer of the solution of thickness 1 mm, 2 mm or 5 mm was formed, and cooled to about −5 to 0° C. The cooled aqueous BSA solution was frozen at −50 to −40° C. by a freeze-dryer (Triomaster A04: Kyowa Vacuum (condensation capacity 10 kg type)) to prepare a freeze-dried powder (hereinafter abbreviated as BSA powder). By using the resulting BSA powder, the average particle size of the finely divided BSA powder was measured according to the same manner as that described in Example 1.

Table 10 shows the average particle size of the finely divided BSA powder obtained by freezing the aqueous BSA solution of Formulation 1 according to the above process. The mean cooling rate of the above freeze-drying became above −2.1 C./min. to −1.6° C./min. and the average particle size of the resulting finely divided BAS powder was 28.9 to 35.0 μm.

TABLE 10

|  | Thickness of layer | | |
| --- | --- | --- | --- |
|  | 1 mm | 2 mm | 5 mm |
| Average particle size (μm) | 35.0 | 38.9 | 28.9 |
| Mean cooling rate (° C./min.) | −2.1 | −1.6 | −2.1 |

Reference Example 2

Freeze-vacuum Drying of Aqueous BSA Solution

The aqueous BSA solution of Formulation 1 was prepared. The solution was added to a tray so that a layer of the solution of thickness 1 mm was formed and placed in a freeze-dryer (Triomaster A04: Kyowa Vacuum (condensation capacity 10 kg type)). The temperature of the solution was controlled to 0° C. Then, the freeze-dryer shelf was cooled at a cooling rate of −4° C./hr. to freeze the BSA solution, followed by freeze-drying to prepare a BSA powder. By using the resulting BSA powder, the average particle size of the finely divided BSA powder was measured according to the same manner as that described in Example 1.

Table 11 shows the average particle size of the finely divided BSA powder obtained by freezing the aqueous BSA solution of Formulation 1 according to the above process. The mean cooling rate of the above freeze-drying is the same as that of the freeze-dryer shelf, i.e., −4° C./hr. At this time, the average particle size of the resulting finely divided BAS powder was 32.5 μm.

TABLE 11

|  | Thickness of layer 1 mm |
| --- | --- |
| Average particle size (μm) | 32.5 |
| Mean cooling rate (° C./hr.) | −4 |

As a result of the comparison of Examples 1 to 6C with Reference Examples 1 and 2, it has been confirmed that, as the cooling rate is slower, the average particle size of the finely divided protein powder becomes larger.

Example 7

Freezing of Aqueous hGH Solution and Subsequent Vacuum Drying

The aqueous hGH solution of Formulation 2 was prepared. The solution was adjusted to room temperature and given amount portions thereof were sprayed intermittently to a tray (area: about 1,300 cm²) on a freeze-dryer shelf cooled at below −25° C., and freeze-dried (Triomaster A04: Kyowa Vacuum (condensation capacity 10 kg type)) to prepare a hGH powder. By using the hGH powder, the average particle size of the finely divided hGH powder was measured according to the same manner as that described in Example 1.

Table 12 shows the average particle size of the finely divided hGH powder obtained by freezing Formulation 2 according to the above process. When the rate of spraying Formulation 2 to the tray was controlled to 50 mL/5 min. to 100 mL/5 min., the mean cooling rate of Formulation 2 became −65.3° C. (maximum −73.9° C./min.) to −37.3° C./min. (minimum −34.3° C./min.) and it was possible to control the average particle size of the finely divided hGH powder to 1.5 μm to 9.5 μm by controlling the dropping rate to 60 mL/5 min. to 140 mL/5 min.

TABLE 12

|  | Spraying rate (amount (mL) per 5 min./tray) | | |
| --- | --- | --- | --- |
|  | 50 | 80 | 100 |
| Average particle size (μm) | 1.5 | 2.9 | 9.5 |
| Mean cooling rate (° C./min.) | −65.3 | −43.3 | −37.3 |

Example 8

Production of Microcapsules Including hGH

To a solution of 1.85 g of a lactic acid/glycolic acid copolymer (lactic acid/glycol acid=50/50, average molecular weight as converted value to polystyrene=13,000, viscosity=0.145 dL/g) and 10 mg of zinc oxide in 2.7 mL of dichloromethane was added 140 mg of the hGH powder obtained in Example 3, the amount of application of 10 or 60 (amount for 5 min. (mL) per tray). Then, it was atomized by using Polytron (commercially available from Kinemachica). The S/O dispersion was added to 800 mL of an aqueous solution of 0.1% polyvinyl alcohol. Then, the resulting liquid was stirred and emulsified using a homomixer. Dichloromethane was evaporated with stirring for 3 hours at room temperature and then the dispersion was centrifuged (about 1,800 rpm) to collect microcapsules. Subsequently, the microcapsules were washed 2 times with 400 mL of distilled water, followed by addition of 0.2 g of D-mannitol and then freeze-drying. Further, the resulting substance was dried in vacuo at 46° C. for 3 days for removing the remaining solvent. Thus, 2 kinds of microcapsules including hGH were obtained.

Example 9

Production of Microcapsules Including hGH

According to the same manner as that described in Example 8, 2 kinds of microcapsules including hGH were obtained by using the hGH powder prepared in Example 7, the spraying amount of 50 and 80 (amount for 5 min. (mL)/tray).

Example 10

Production of Microcapsules Including hGH

To a solution of 1.69 g of a lactic acid/glycolic acid copolymer (lactic acid/glycol acid (molar ratio)=about 65/35, average molecular weight as converted value to polystyrene=about 14,500) and 10 mg of zinc oxide in 2.7 mL of dichloromethane was added 300 mg of the hGH powder obtained by freezing Formulation 2 of Example 6B at a dropping rate of 94 mL/5 min (amount to be contacted: 250 mL) and then drying. Then, it was atomized by using Polytron (commercially available from Kinemachica). The S/O dispersion was added to 800 mL of an aqueous solution of 0.1% polyvinyl alcohol. Then, the resulting liquid was stirred and emulsified using a homomixer. Dichloromethane was evaporated with stirring for 3 hours at room temperature and then the dispersion was centrifuged (about 1,800 rpm) to collect microcapsules. Subsequently, the microcapsules were washed 2 times with 400 mL of distilled water, followed by addition of 0.2 g of D-mannitol and then freeze-drying. Further, the resulting substance was dried in vacuo at 46° C. for 3 days for removing the remaining solvent to obtain microcapsules including hGH.

Example 11

Production of Microcapsules Including hGH

To a solution of 1.69 g of a lactic acid/glycolic acid copolymer (lactic acid/glycol acid (molar ratio)=about 65/35, average molecular weight as converted value to polystyrene=about 14,500) and 10 mg of zinc oxide in 2.7 ml of dichloromethane was added 300 mg of the hGH powder obtained by freezing Formulation 3 of Example 6B at a dropping rate of 80 mL/5 min. (amount to be contacted: 100 mL) and drying. Then, it was atomized by using Polytron (commercially available from Kinemachica). The S/O dispersion was added to 800 mL of an aqueous solution of 0.1% polyvinyl alcohol. Then, the resulting liquid was stirred and emulsified using a homomixer. Dichloromethane was evaporated with stirring for 3 hours at room temperature and then the dispersion was centrifuged (about 1,800 rpm) to collect microcapsules. Subsequently, the microcapsules were washed 2 times with 400 mL of distilled water, followed by addition of 0.2 g of D-mannitol and then freeze-drying. Further, the resulting substance was dried in vacuo at 46° C. for 3 days for removing the remaining solvent to obtain microcapsules including hGH.

Example 12

Production of Microcapsules Including hGH

To a solution of 1.69 g of a lactic acid/glycolic acid copolymer (lactic acid/glycol acid (molar ratio)=about 65/35, average molecular weight as converted value to polystyrene=about 14,500) and 10 mg of zinc oxide in 2.565 mL of dichloromethane was added 300 mg of the hGH powder obtained by freezing Formulation 2 of Example 6B at a dropping rate of 94 mL/5 min. (amount to be contacted: 250 mL) and drying. Then, 0.135 mL of ethanol was added and the mixture was atomized by using Polytron (commercially available from Kinemachica). The S/O dispersion was added to 800 mL of an aqueous solution of 0.1% polyvinyl alcohol. Then, the resulting liquid was stirred and emulsified using a homomixer. Dichloromethane was evaporated with stirring for 3 hours at room temperature and then the dispersion was centrifuged (about 1,800 rpm) to collect microcapsules. Subsequently, the microcapsules were washed 2 times with 400 mL of distilled water, followed by addition of 0.2 g of D-mannitol and then freeze-drying. Further, the resulting substance was dried in vacuo at 46° C. for 3 days for removing the remaining solvent to obtain microcapsules including hGH.

Experimental Example 1

In Vivo Release Profile

The microcapsules obtained in Examples 8 and 9 were subcutaneously administered to immuno-suppressed SD rats (male, aged 6 weeks) (6 mg as amount of hGH/rat). Then, rat blood was serially collected as time passed. The serum hGH level was measured by the radioimmunoassay (commercially available under the name of Ab beads HGH from EIKEN CHEMICAL CO., LTD.) to evaluate the hGH release profile. The immuno-suppressed SD rat was prepared by subcutaneous injection of Prograf™ (commercially available from Fujisawa Pharmaceutical Co., Ltd.) in the amounts of 0.4 mg/rat 3 days before the first administration of the microcapsules, of 0.2 mg/rat at the time of the first administration, and of 0.2 mg/rat on 4th day, 7th day, 11th day and 14th day after the first administration. The results are shown in FIG. 1.

As obviously understood from the results of FIG. 1, the blood hGH level after administration of the microcapsules prepared by using the hGH powder obtained by application is higher than that after administration of the microcapsules prepared by using the powder obtained by spraying. These results show that the microcapsule preparation prepared by using the hGH powder obtained by application has higher bioavailability.

Experimental Example 2

Analysis of Higher-order Structure of Finely Divided Protein Powder by FT-IR

Two kinds of hGH powders, i.e., hGH powder obtained in Example 4, the amount of application of 80 (amount for 5 min. (mL)/tray) and hGH powder obtained in Example 7, the spraying amount of 80 (amount for 5 min. (mL)/tray), were subjected to analysis of higher-order structures thereof by FT-IR (Journal of Pharmaceutical Science, Vol. 87, pp. 1412–1420 (1998)). The results are shown in Table 13 as the mean±S.D. (n=3). As seen from Table 13, the α-helix content of hGH powder obtained in Example 4 by application is much higher than that of hGH powder obtained in Example 7 by spraying. Since the α-helix content of hGH in heavy water was 59%, the hGH powder obtained in Example 7 by spraying retained 39% of α-helix in comparison with the α-helix content in heavy water. On the other hand, the hGH powder obtained in Example 4 by application retained 59% of α-helix in comparison with the α-helix content in heavy water.

TABLE 13

| Example 4 Application amount: amount for 5 min. 80 mL/tray | | Example 7 Spray amount: amount for 5 min. 80 ml/tray | | |
| --- | --- | --- | --- | --- |
| wavelength (cm⁻¹) | ratio | wavelength (cm⁻¹) | ratio | assignment |
| 1694.3 ± 0.3 | 3.5 ± 1.3 | 1694.3 ± 0.2 | 3.5 ± 0.4 | β-sheet |
| 1682.9 ± 0.6 | 18.9 ± 0.4 | 1684.8 ± 0.1 | 13.7 ± 0.2 | unordered |
| 1667.3 ± 1.8 | 22.3 ± 0.9 | 1666.9 ± 0.6 | 35.7 ± 1.7 | unordered |
| 1654.7 ± 0.6 | 31.2 ± 2.0 | 1653.5 ± 0.2 | 23.3 ± 2.0 | α-helix |
| 1641.5 ± 0.4 | 14.6 ± 0.7 | 1641.8 ± 0.3 | 13.8 ± 0.7 | unordered |
| 1630.1 ± 0.3 | 6.0 ± 0.9 | 1630.7 ± 0.4 | 6.5 ± 0.7 | β-sheet |
| 1615.8 ± 0.2 | 3.6 ± 0.1 | 1615.8 ± 0.1 | 3.5 ± 0.1 | unordered |

Industrial Applicability

According to the present invention, a stable protein powder which retains its higher-order structure at a high level can be simply and conveniently produced without bringing into contact with liquefied gas. Therefore, in comparison with a process for producing a finely divided protein powder by spraying a protein-containing solution in liquefied gas to freeze the solution and then drying, large scale and expensive facilities are not required for coping with heat insulation and expansion and contraction of materials of an apparatus due to difference in temperature, maintaining aseptic conditions, evacuating the liquefied gas, etc.

Further, the protein powder obtained by the present invention can be converted into a finely divided protein powder by simple and convenient atomization treatment and, by using the finely divided protein powder, there can be provided a sustained-release preparation which provides a stable high blood level of the protein over a long period of time.

In addition, when a growth hormone-containing preparation is produced by using a lactic acid-glycolic acid copolymer having a molar ratio of lactic acid and glycolic acid of about 60:40 to 70:30 as a base material, a sustained-release preparation which can release growth hormone over about one month can be produced.

What is claimed is:

1. A process for producing a protein powder which comprises applying or dropping a protein-containing solution on a refrigerant carrier, freezing the solution at a cooling rate of about −300 to −10° C./min., and then drying the frozen solution.

2. The process according to claim 1, wherein the protein-containing solution is applied or dropped having a diameter of about 0.1 to 40 mm.

3. The process according to claim 1, wherein freezing is carried out by preventing the protein-containing solution from direct contact with a liquid refrigerant.

4. The process according to claim 1, wherein a volatile salt or water-miscible organic solvent is added to the protein-containing solution.

5. The process according to claim 4, wherein the volatile salt is ammonium acetate.

6. A protein powder obtained by the process according to claim 1.

7. The protein powder according to claim 6, wherein the protein has a molecular weight of about 5,000 to 1,000,000 dalton.

8. The protein powder according to claim 6, wherein the protein is selected from hormones, cytokines, hematopoietic factors, growth factors and enzymes.

9. The protein powder according to claim 6, wherein the protein is a growth hormone or insulin.

10. The protein powder according to claim 6, wherein the protein retains 45% or more of α-helix based on the total α-helix content in the protein-containing solution.

11. A process for producing a finely divided protein powder which comprises atomizing the protein powder according to claim 6.

12. The process according to claim 11, wherein the atomization is carried out so that a finely divided protein powder having an average particle size of about 0.5 to 20 μm is obtained.

13. A sustained-release preparation which comprises the finely divided protein powder obtained by the process according to claim 11 and a base material.

14. The sustained-release preparation according to claim 13, wherein the base material of the sustained-release preparation is a material derived from a living body or a synthetic polymer.

15. The sustained-release preparation according to claim 14, wherein the material derived from a living body or a synthetic polymer is a biodegradable polymer.

16. A process for producing a sustained-release preparation which comprises mixing the finely divided protein powder obtained by the process according to claim 11 with a base material.

* * * * *

UNITED STATES PATENT AND TRADEMARK OFFICE
CERTIFICATE OF CORRECTION

PATENT NO.    : 6,723,347 B1
DATED         : April 20, 2004
INVENTOR(S)   : Yutaka Yamagata et al.

It is certified that error appears in the above-identified patent and that said Letters Patent is hereby corrected as shown below:

<u>Title page,</u>
Item [75], Inventors, please change "Nishimoniya (JP)" to -- Nishinomiya (JP) --.
Item [*] Notice, please insert the following:
-- This patent is subject to a Terminal Disclaimer. --

Signed and Sealed this

Twenty-second Day of February, 2005

JON W. DUDAS
*Director of the United States Patent and Trademark Office*